United States Patent [19]
Willeke et al.

[11] Patent Number: 5,958,111
[45] Date of Patent: Sep. 28, 1999

[54] METHOD FOR SAMPLING AEROSOLS

[75] Inventors: Klaus Willeke; Sergey A. Grinshpun, both of Cincinnati, Ohio

[73] Assignee: SKC, Inc., Eighty Four, Pa.

[21] Appl. No.: 08/859,492

[22] Filed: May 20, 1997

Related U.S. Application Data

[63] Continuation-in-part of application No. 08/638,224, Apr. 26, 1996, abandoned.

[51] Int. Cl.$^6$ ....................................................... B01D 46/42
[52] U.S. Cl. .................................................. 95/268; 55/320
[58] Field of Search ................................ 95/268; 55/320, 55/329, 331, 332, 336, 463, 419, 521

[56] References Cited

U.S. PATENT DOCUMENTS

| | | | |
|---|---|---|---|
| 4,157,902 | 6/1979 | Tokar | 55/331 X |
| 4,606,743 | 8/1986 | Shuman | 55/336 X |
| 5,248,323 | 9/1993 | Stevenson | 95/268 X |

OTHER PUBLICATIONS

Suresh Kalatoor, Sergey Grinshpun and Klaus Willeke: "New Aerosol Sampler with Low Wind Sensitivity and Good Filter Collection Uniformity" Atmospheric Environment 29, No. 10 pp. 1105–1112, Jun. 19, 1995.

Primary Examiner—Richard L. Chiesa
Attorney, Agent, or Firm—William L. Krayer

[57] ABSTRACT

A method for the collection of solid or liquid particles suspended in air (aerosol). The method involves abstracting a quantity of air through a curved, porous plate with evenly spaced holes which are designed to give an accurate sample of the particle content over defined size ranges. This method differs from similar methods in that it (1) provides a minimal bias in the results from the effects of ambient air velocity or direction, (2) provides a more even distribution of particles over a collection medium, and (3) enables exclusion of particles exceeding defined upper size limits.

7 Claims, 9 Drawing Sheets

METHOD FOR SAMPLING AEROSOLS

CROSS-REFERENCE TO RELATED APPLICATION

This is a continuation-in-part of application Ser. No. 08/638,224 filed Apr. 26, 1996, now abandoned. Applicants claim the benefit of 35USC120 with respect to all subject matter in this application common to said application Ser. No. 08/638,224.

The present invention relates to the accurate collection of solid or liquid particles suspended in air (aerosol) with low wind velocity sensitivity, good filter collection uniformity, and definable size exclusion capabilities.

BACKGROUND OF THE INVENTION

1. Field of the Invention

A standard technique for assessing solid or liquid aerosol concentrations is by abstracting a quantity of air and measuring the aerosol fraction. The aerosol can be measured by a variety of methods. One method is to collect the aerosol fraction of the air sample on a filter, with either subsequent determination of collected mass, examination by microscopy, or analysis by chemical methods. Other methods for aerosol measurement involve the use of sensors, but in most cases the principle of sample abstraction is the same. The flow rate through a sampler is usually established according to the specifications of the sampling method and is held constant so that an accurate sample and representative volume can be determined. Stationary aerosol samplers are used to evaluate both outdoor and indoor environments including work-places. Personal breathing zone samplers worn by workers are used to estimate their exposures to workplace pollutants. The inlets of commercially available samplers have evolved to measure the aerosol concentrations in different environments. Significant biases (primarily particle losses) may occur during aspiration into a sampler and during transmission of aerosols through the sampler. These biases are sensitive to the magnitude and direction of the ambient air velocity. In indoor work environments, where the air velocity typically ranges from 100 to 300 cm s$^{-1}$, the external geometry of a sampling cassette may influence the flow pattern in the vicinity of the sampler's inlet, thereby adversely affecting the sampler's performance.

The sampling efficiency of a sampler, $E_s$ is defined as the ratio of the sampled particle concentration, $C_s$, to the environmental particle concentration, $C_o$ $$E_s = C_s/C_o \quad (1)$$

To determine $C_o$, it is important that the inlet efficiency be evaluated under a range of controlled operating conditions. Particle size distribution, wind velocity $U_w$, inlet velocity $U_i$, inlet shape, particle density, and inlet orientation with respect to the wind and gravitational force are some of the factors which affect sampling efficiency.

For isoaxial sampling, the velocity ratio R, which is the ratio of the wind to the inlet velocity, determines whether the sampling is isokinetic (R=1), subisokinetic (R>1) or super-isokinetic (R<1). During isokinetic sampling, the limiting stream-surface flows into the inlet without a change in direction, and the particle concentration at the face of the inlet is equal to $C_o$. During non-isokinetic aspiration, particle inertia may lead to the migration of some particles across the limiting stream-surface, resulting in a different aerosol concentration at the face of the inlet.

For the simple case of a tubular, thin-walled inlet, overall sampling efficiency consists of two major components—aspiration efficiency, $E_a$, and transmission efficiency, $E_t$:

$$E_s = E_a E_t \quad (2)$$

Because of the complex geometry of many aerosol samplers and the unstable wind conditions present in most environments, it is usually difficult to exactly quantify sampling efficiency.

The main purpose of a well-designed sampler is to ensure that all or most of the particles in a given volume of ambient air are aspirated to the inlet and reliably transported onto a filter or through a dynamic sensor for analysis. The external geometry of the sampler may significantly affect aspiration efficiency. Particles may be lost during transmission through the sampler due to one or more physical mechanisms, such as direct wall impaction and gravitational settling, migration in the developing boundary layer, and electrostatic deposition. The main reason for such particle losses in the entrance region of a sampling inlet is the formation of a vena contract (for R<1) and impaction of particles to the inner wall of the inlet. Thus, the concentration of particles collected on a filter or passed through a sensor is generally less than the aspirated particle concentration.

If there is a long distance between the entrance region and the sensor or collection surface, additional losses may occur, mainly due to gravitational settling and electrostatic deposition of particles. Gravitational settling depends on particle settling velocity and the distance from the inlet face to the filter or sensor surface. Electrostatic deposition depends on the electric charge on the particles and the electrical conductivity of the sampler's surface. The combination of these effects leads to non-uniform deposition of particles across a collection filter, which can lead to significant biases in the measurement of the deposited aerosol, e.g. from microscopic evaluation of selected portions of the filter.

In workplace environments, the protection of the workers' health is of primary importance and as such the size and concentration of the particles that can be inhaled by a person is of concern. International conventions have been agreed concerning the aspiration efficiency of different size particles in different portions of the human airway system, thus fostering the development of samplers that show similar aspiration efficiencies. Rather than attempting to sample "total dust", optimum sampling is defined on the basis of the efficiency of human breathing. The sampling efficiency for particles larger than 30 $\mu$m was set at 50%. However, only limited information is available regarding the collection efficiency of particles larger than 20 $\mu$m for currently used samplers.

2. Description of Related Art

No US or foreign patent documents have been found with related claims. No patent document was found for the closed-face 25 mm filter cassette with which data were taken for comparison, shown in FIGS. 4a–4f.

SUMMARY OF THE INVENTION

A method for the collection of solid or liquid particles suspended in air (aerosol). The method involves abstracting a quantity of air through a curved porous plate, where the angle of curvature of the plate, and the size and number of the holes comprising the porosity are designed to allow accurate sampling of the particulate content over defined size ranges. This method differs from similar methods in that it (1) provides a minimal bias in the results from the effects of ambient air velocity or direction, (2) provides a more even distribution of particles over a collection medium, and (3) enables exclusion of particles exceeding defined upper size limits.

BRIEF DESCRIPTION OF THE DRAWINGS

FIG. 3A shows the sampler facing horizontal air flow, $\Theta=0°$. FIG. 3B shows the sampler facing downward, $\Theta=90°$.

DESCRIPTION OF THE PREFERRED EMBODIMENTS

1. A method for sampling aerosols from an air environment into an interior space, said method having low sensitivity to the flow direction and velocity of the airborne particles and comprising the steps of:

(1) air and airborne particles, herein referred to as aerosol, being drawn towards a curved porous plate;

(2) said air and all or a fraction of said particles flowing through said holes of said curved, porous plate, the plate thus acting as a porous surface for wind-insensitive particle sampling and, whenever desired, as a barrier that keeps out particles in a size-selective manner, thus satisfying specific size-selective sampling criteria;

(3) said air flow through said holes creating a pressure drop;

(4) said particles entering a chamber to which said curved, porous plate is attached; and (5) said chamber being connected to a vacuum or suction source for drawing the aerosol through said curved, porous plate.

2. The method for sampling aerosols as defined in (1) wherein the step of aerosol flow through the curved, porous plate comprises a curved surface that is spherical or close-to spherical with a subtended angle between 90 and 270°.

3. The method for sampling aerosols as defined in (1) wherein the step of aerosol flow through the curved, porous plate comprises a plate with a porosity of between 1% and 60%.

4. The method for sampling aerosols as defined in (1) wherein the step of aerosol flow through the curved, porous plate comprises a plate with uniformly or close-to-uniformly spaced holes between 10 $\mu$m and 1 mm in diameter.

5. The method for sampling aerosols as defined in (1) wherein the step of aerosol flow through the curved, porous plate comprises a plate across which the pressure drop is between 0.04 inch (1 mm) and 40 inch (100 cm) water gauge.

6. The method for sampling aerosols as defined in (1) wherein the step of aerosol flow through the curved, porous plate comprises particles between 0.001 $\mu$m and 100 $\mu$m.

7. The method for sampling aerosols as defined in (1) wherein the step of aerosol flow through the curved, porous plate comprises a flow rate between 0.1 and 300 1 min$^{-1}$.

Figure 1:
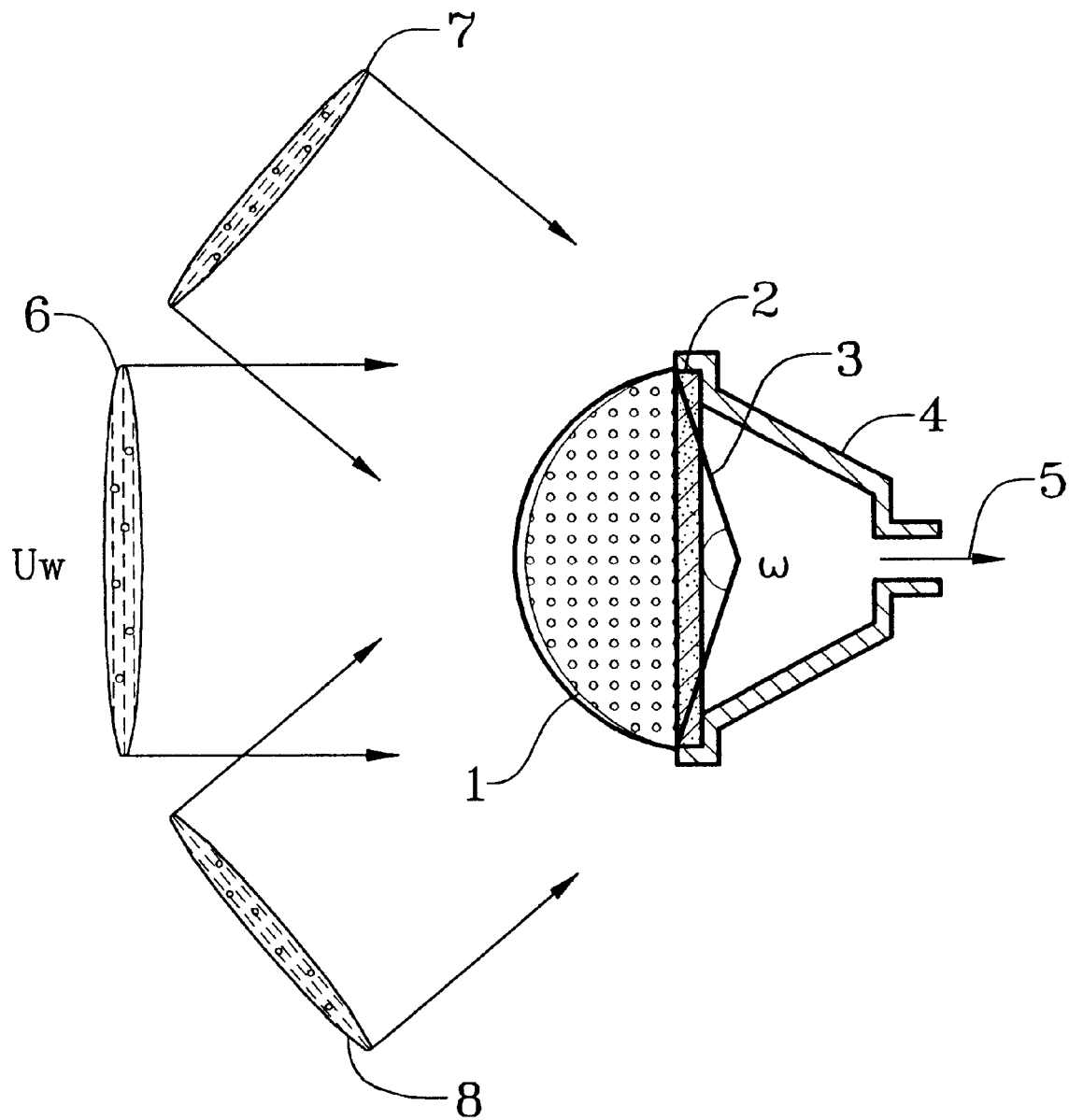
FIG. 1 shows the schematic diagram of an aerosol sampler with multi-directional sampling capability based on the method described in this invention.
Figure 2A:
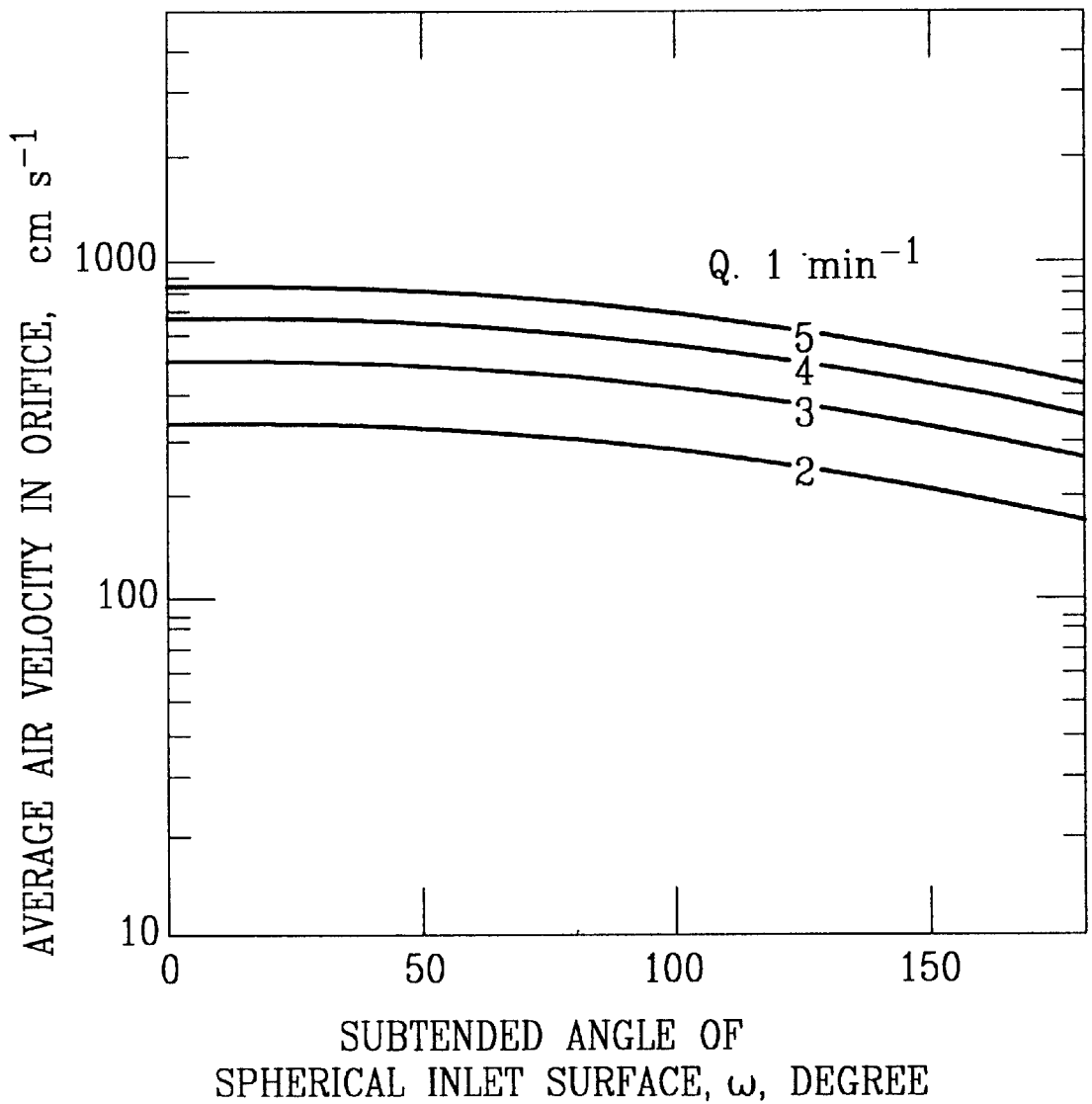
FIGS. 2A, 2B, 2C and 2D show calculated air velocities in evenly spread circular orifices in a spherical inlet surface, filter diameter=25 mm.
Figure 2B:
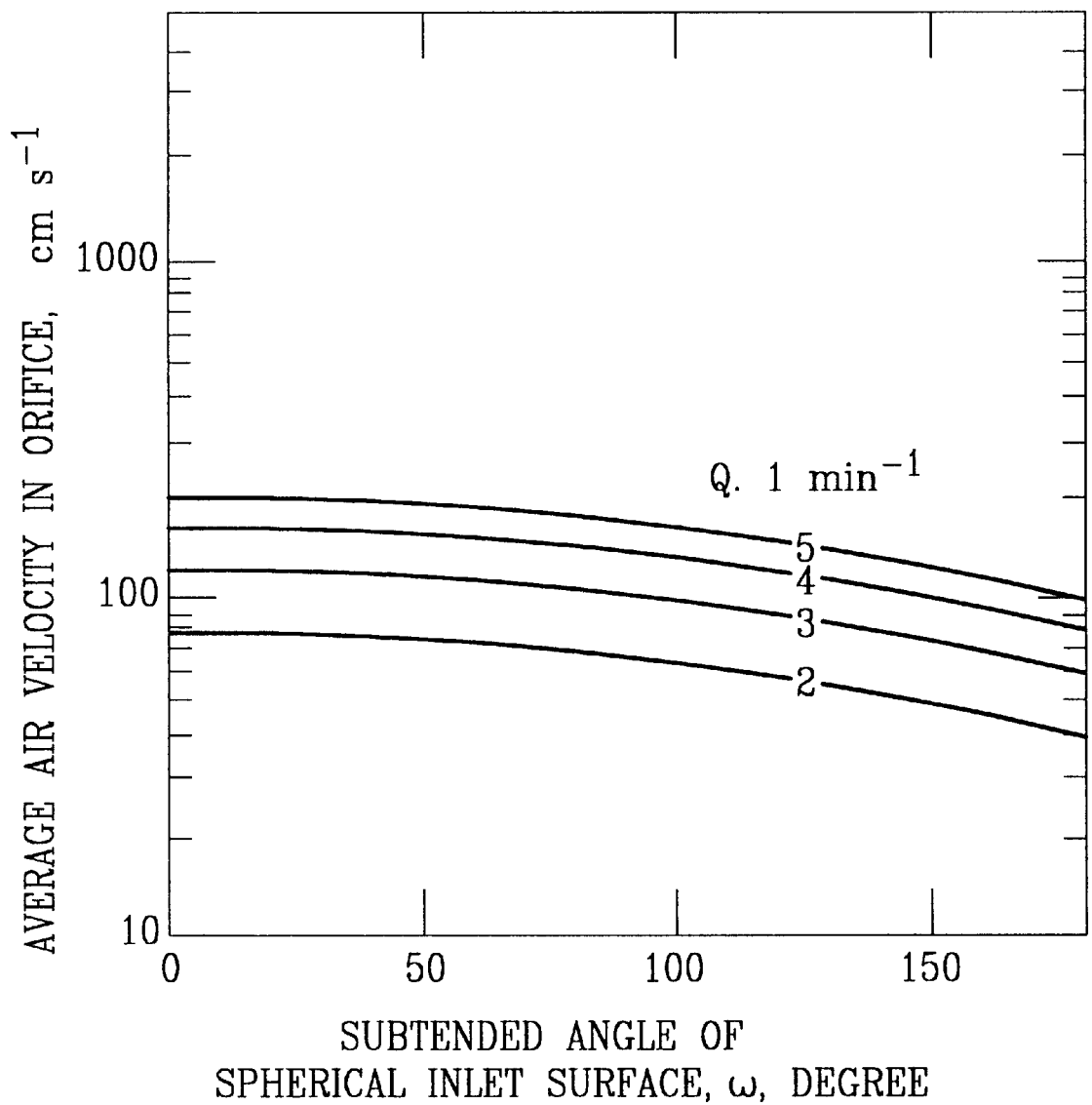
Figure 2C:
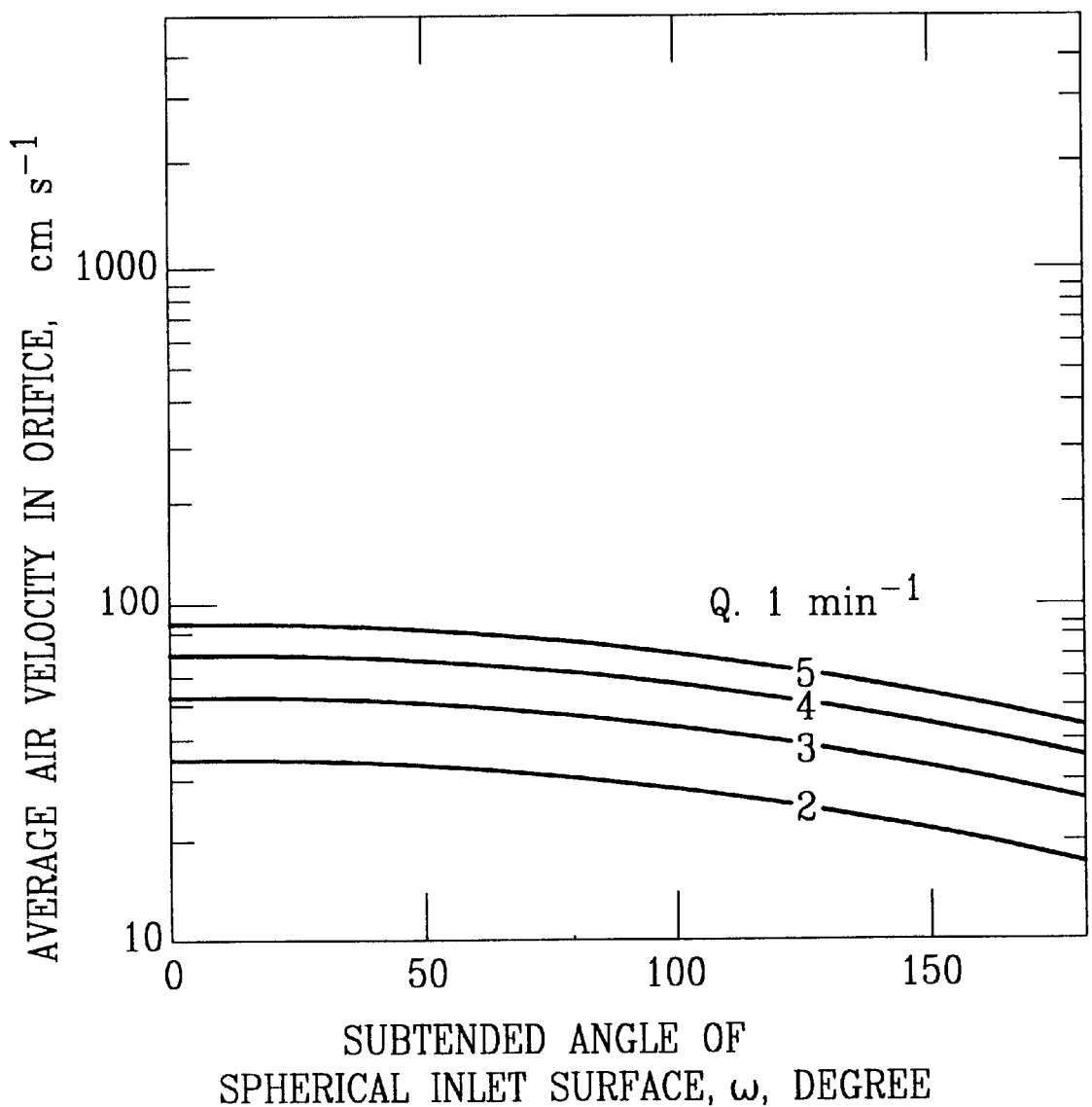
Figure 2D:
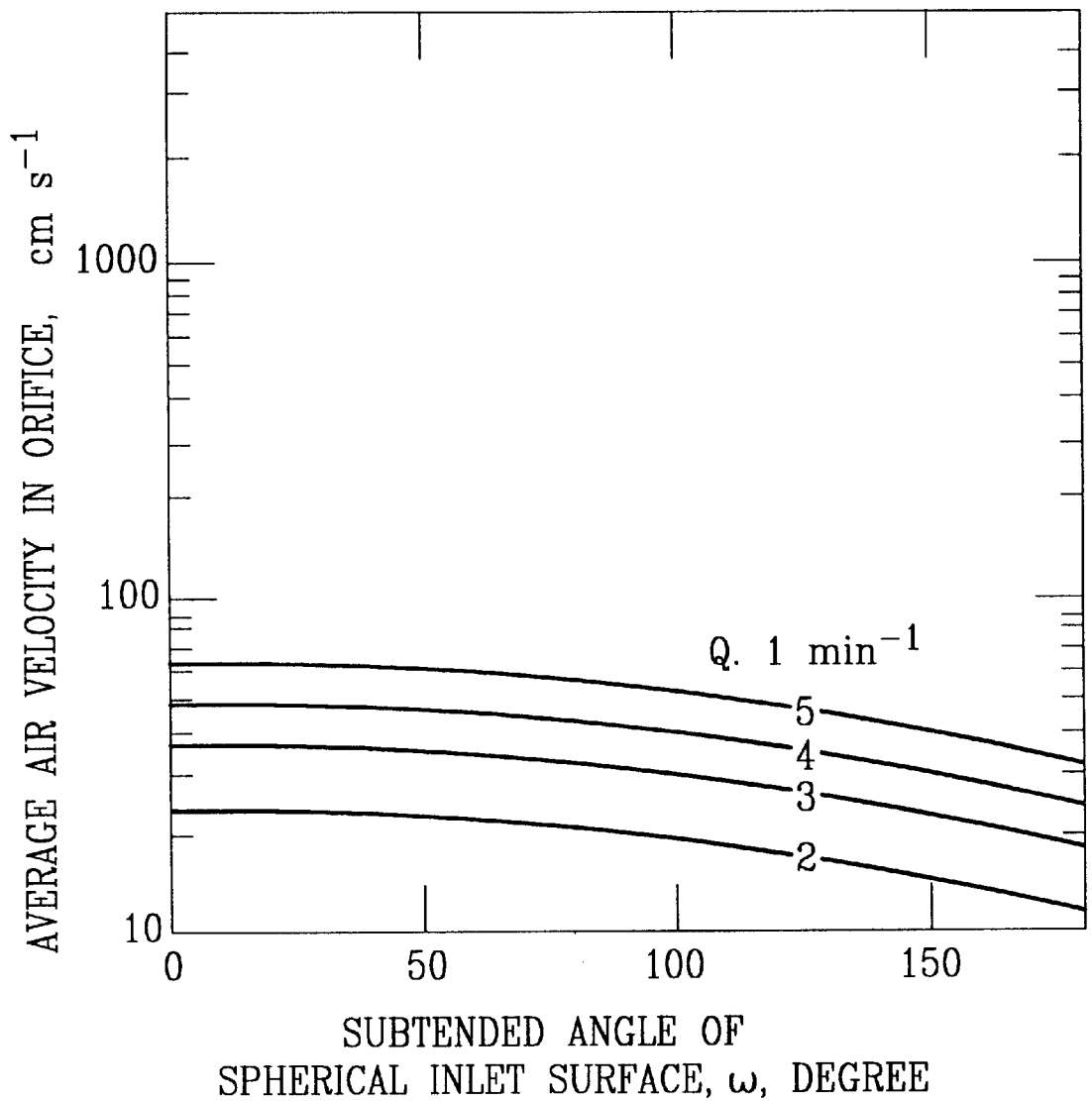

One embodiment of a sampler based on this method is schematically shown in FIG. 1. Inlet (1) is formed from a portion of a spherical shell with numerous, identical, evenly spaced holes that act as sampling orifices and give the sampler multidirectional sampling capability. The parameters that were considered while designing the sampler were the subtended angle (3) of the spherical surface ($\omega$, filter diameter, porosity of the spherical surface, orifice diameter and sampling flow rate. Filter (2), held in housing (4), is directly behind the inlet to avoid transmission losses in the sampler. The uniform distribution of the orifices on the curved inlet surface contributes to the uniform distribution of sampled particles on the filter surface. (6), (7), and (8) show multi-directional flow sampling capability.

This design can be used for ambient air sampling and for personal breathing zone sampling. For the latter, the airflow is withdrawn laterally after the filter (90° to the outlet port (5) in FIG. 1), so that the sampler protrudes a minimum distance from the wearer's clothing. In studies relating to the performance of this embodiment, the following sampling parameters were chosen for workplace environmental conditions: the flow rate was fixed at 2 1 min$^{-1}$ (this is a common flow rate for measuring worker exposure which is readily achievable by personal sampling pumps) and a filter diameter of 25 mm was chosen (this size filter is used in work environment sampling).

The air velocity through the orifice of the curved inlet surface has to be high enough to create enough pressure drop for even flow distribution, and the orifice hole size has to be large enough to allow the largest particles to pass through without significant wall losses caused by interception. Inertial deposition losses on the inlet surface were found to reduce the efficiency of particle penetration through the inlet screen when sampling larger particles. Since this may affect performance characteristics, especially when sampling liquid droplets (when sampling solid particles some of them may bounce from the inlet surface, be re-entrained into the entering airstream and be collected on the filter), the orifice diameters should be at least five times the largest particle diameter tested, i.e. 150 $\mu$m. The physical diameters of the particles used in the study ranged from 13.5 to 30 $\mu$m (corresponding aerodynamic diameter=17–38 $\mu$m). Due to the limitation of the dynamic measurement of particle concentration, larger particles could not be efficiently detected, especially at lower wind velocities. FIGS. 2A, 2B, 2C and 2D show the calculated average air velocities from available metal sheets with different porosity and orifice sizes. As a compromise between inlet velocity and orifice diameter, a metal sheet with 19% porosity and orifice diameters of 254 $\mu$m was formed into a spherical inlet with a subtended angle of 140°. The spherical shell was formed using a specially machined die and a micro-etched stainless steel screen. The average air velocity through these orifices is 25 cm s$^{-1}$ for a 2 1 min$^{-1}$ flow rate through a 25 mm diameter filter, FIG. 2C. The curved inlet was made of steel, since a conductive surface is expected to minimize electrostatic losses when sampling charged particles.

Laboratory Evaluation of the Sampling Method

The performance evaluation of the prototype sampler described under preferred embodiments was conducted in three parts. The first part of the evaluation was flow pattern visualization and quantitative analysis of the sampler aspiration efficiency, which was achieved by determining the limiting streamlines in a two-dimensional p lane using tobacco smoke in a low-velocity wind tunnel. In the second part of the evaluation, overall sampling efficiency was measured for large solid particle s in a horizontal high-velocity aerosol wind tunnel . In the third part, filter deposits were microscopically analyzed for distribution uniformity on the collection surface.

Flow Pattern Visualization and Quantitative Analysis

Figure 3A:
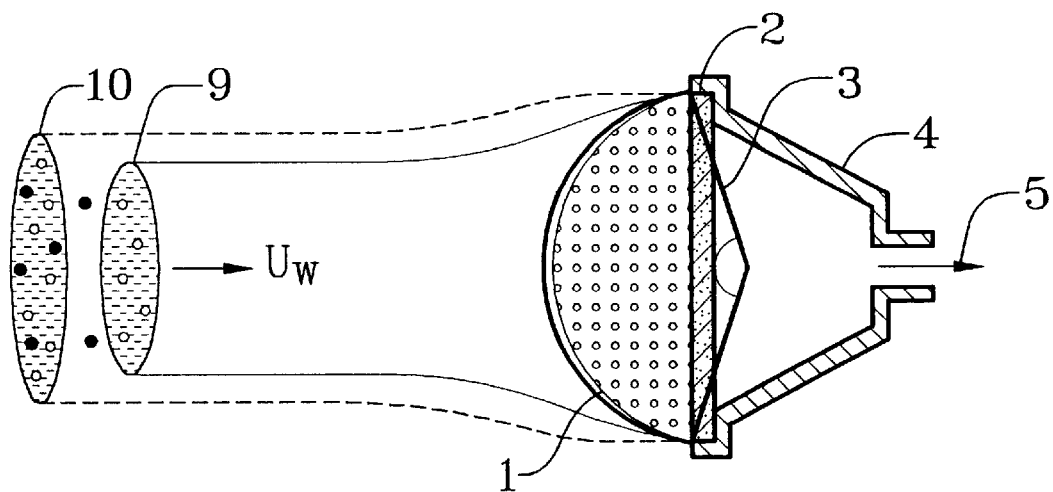
FIGS. 3A and 3B show the schematic representation of the limiting streamlines and particle trajectories for the two inlet orientations.
Figure 3B:
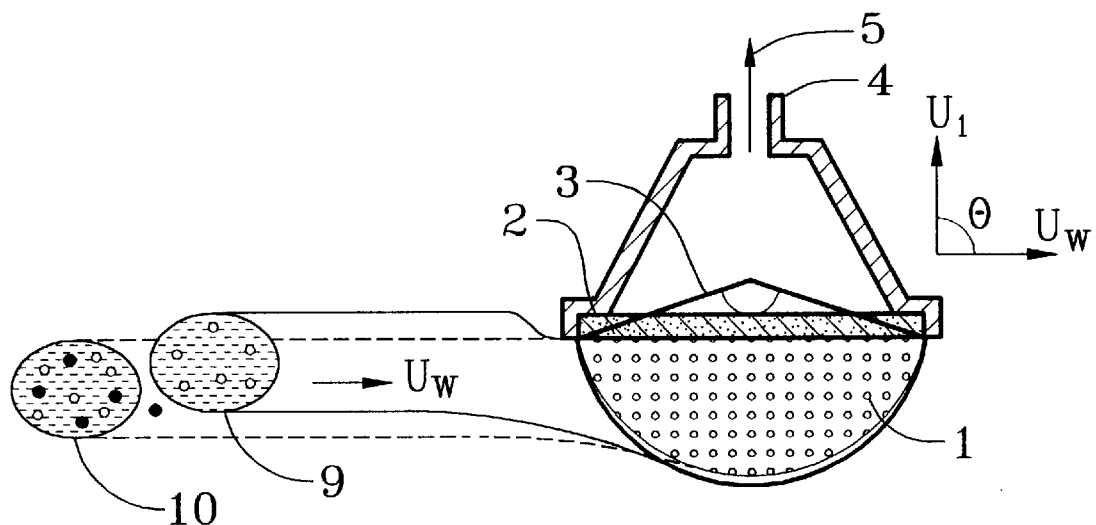
Figures 4A, 4B:
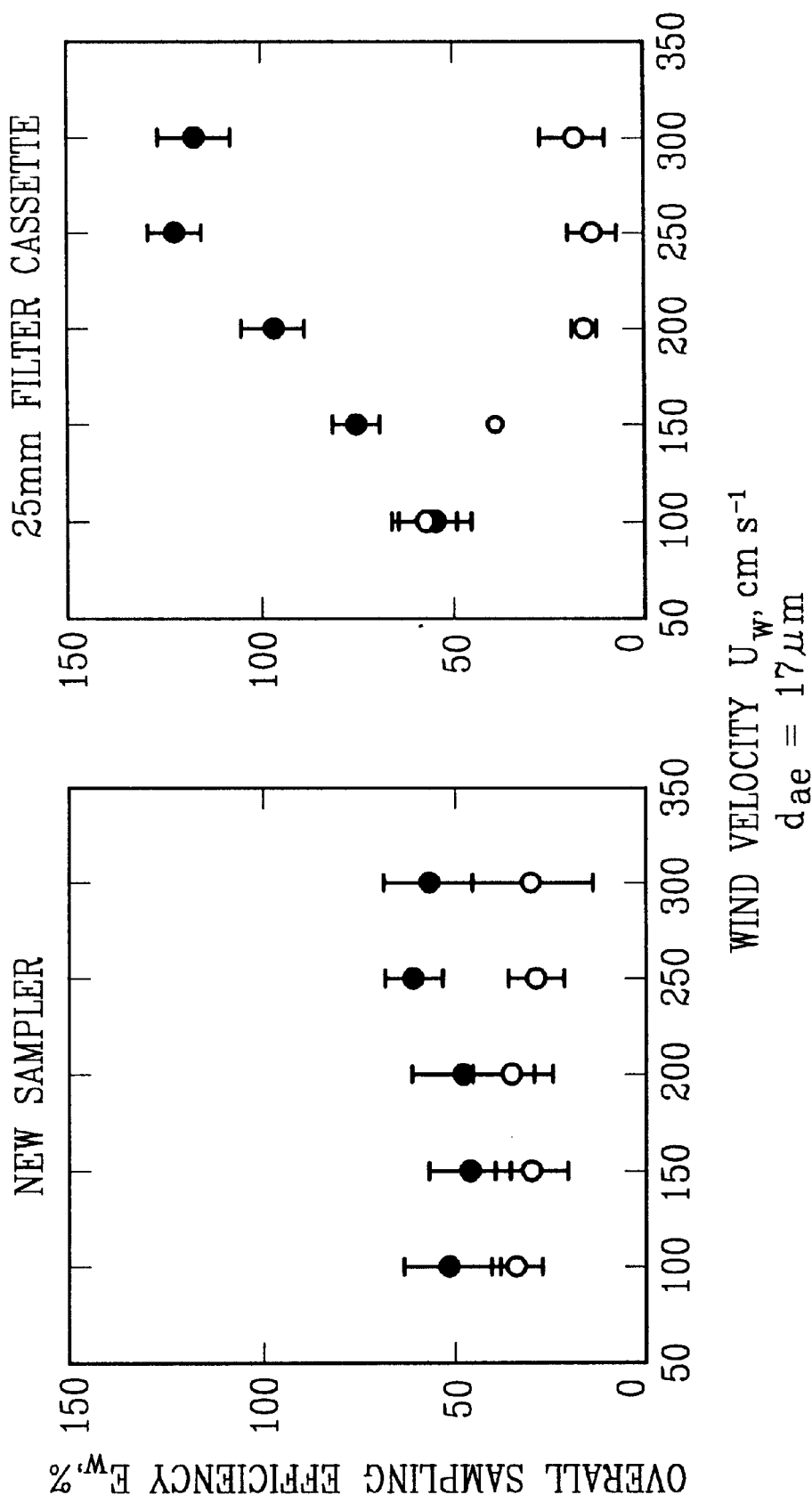
FIGS. 4a–4f show wind-tunnel data of the overall sampling efficiencies for the new sampler and the closed-face 25 mm filter cassette.
Figures 4C, 4D:
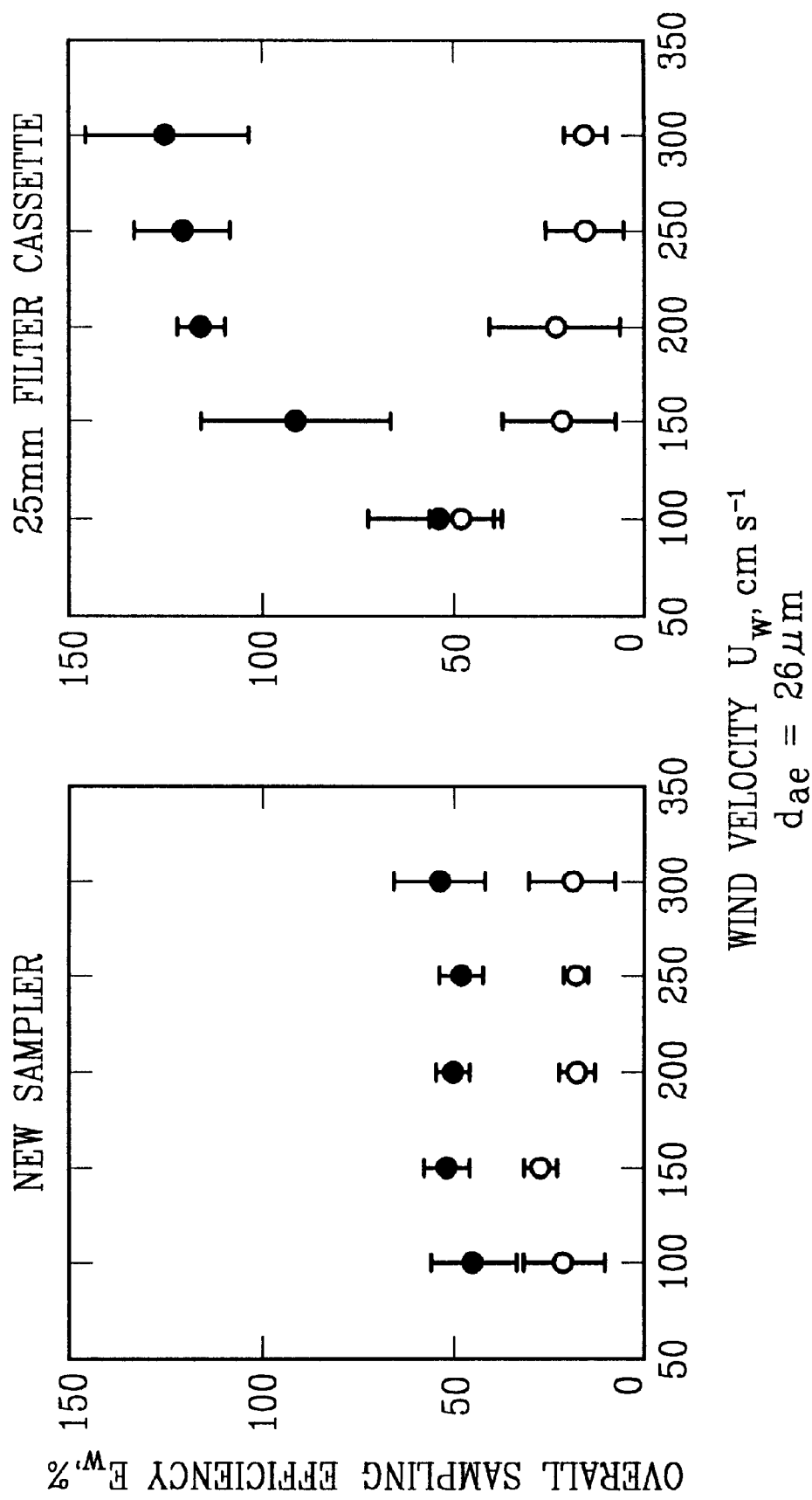
Figures 4E, 4F:
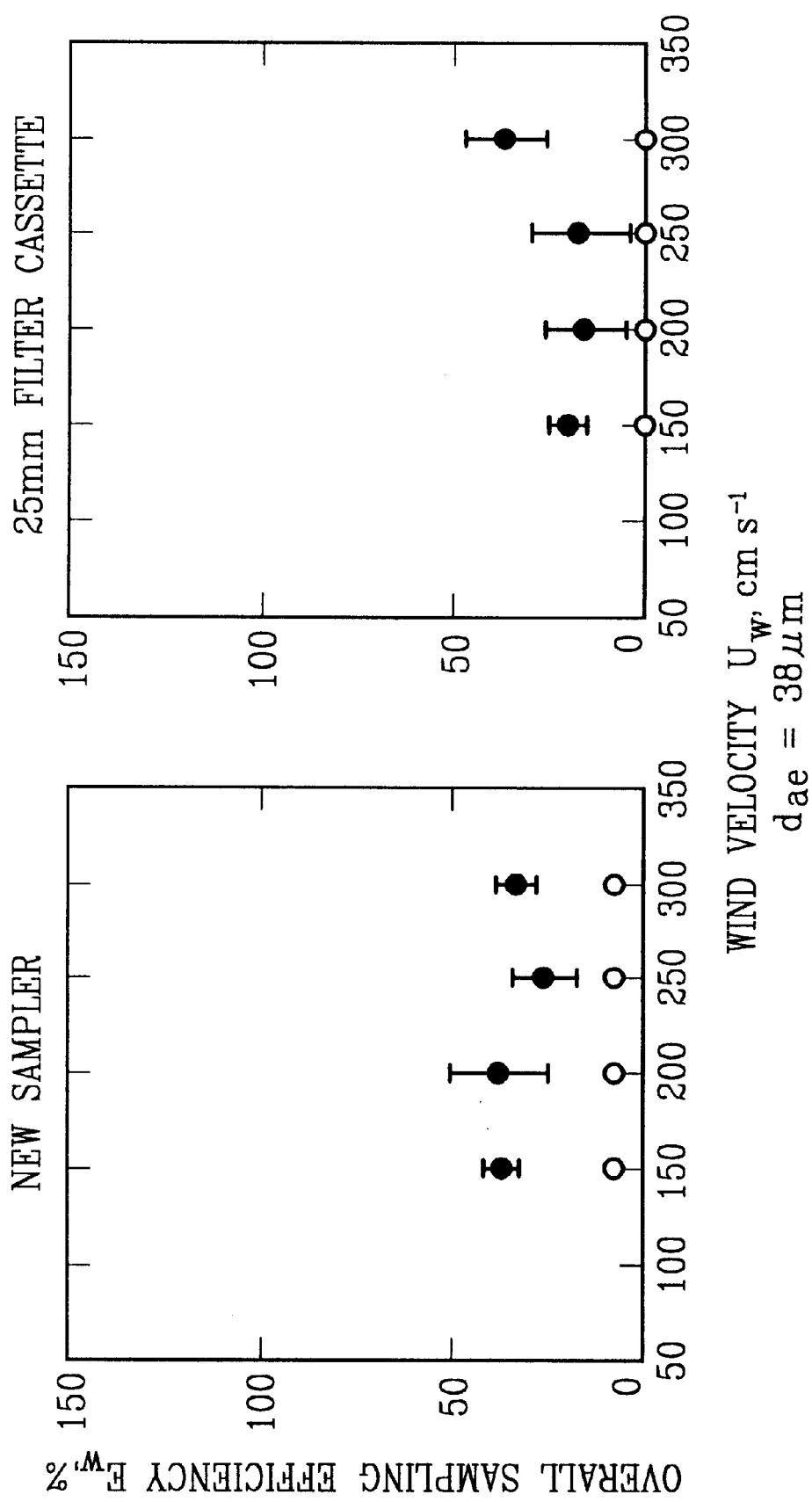

Flow pattern visualization near a sampling inlet and determination of the aspiration efficiency by the limiting streamline method is generally performed only on a sampler with a single opening of either circular or rectangular cross section. We have applied this limiting streamline method to the multiple sampling point surface of the inlet face in order to qualitatively evaluate the turbulence in the sampling zone. The new sampler was tested in a low-velocity wind tunnel with a 20 cm diameter cross-section of transparent plexiglass. A porous foam plug and a honeycomb flow straightener were installed upstream of the sampler to obtain uniform flow in the wind tunnel. A fine stream of tobacco smoke was injected into the test section at a velocity that was approximately equal to that of the wind. A laser beam light sheet illuminated the smoke streamlines, and photographic images were captured on video tape for further analysis. Because the particle size of tobacco smoke is less than 2 $\mu$m, the influence of particle inertia was assumed negligible, and the trajectories of the smoke particles were assumed negligible, and the trajectories of the smoke particles were assumed to equal those of the air streamlines. Two cases of sampler orientation were analyzed, isoaxial ($\Theta=0$) and downward facing ($\Theta=90°$), as schematically shown in FIGS. 3A and 3B. FIG. 3A is with the sampler facing horizontal air flow, $\Theta=0°$ and FIG. 3B is with the sampler facing downward, $\Theta=90°$. (9) represents air and (10) particles to be collected.

For the limiting streamline analysis, the aspiration efficiency, $E_a$, has been defined as $$E_a = \frac{N/V_{air}}{N/V_{particle}} = \frac{V_{particle}}{V_{air}} \quad (3)$$

where N is the number of particles passing through the inlet face, $V_{air}$ is the sampled air volume and $V_{particle}$ is the upstream volume of air from which particles are aspirated. The sampled air volume is related to the upstream cross-sectional area of the limiting streamline surface, $A_{air}$:

$$V_{air} = A_{air} U_w t = A_i U_i t = Qt \quad (4)$$

where $A_i$, is the cross-sectional area of the inlet and Q is the sampling flow rate. Similarly, $$V_{particle} = A_{particle} U_w t \quad (5)$$

where $A_{particle}$ is the upstream cross-sectional area from which particles are aspirated. For inertialess particles, such as the smoke particles used in the tests, $A_{particle}$ is expected to equal $A_{air}$. $A_{particle}$ was measured from the images captured on video tapes for both sampling situations. For isoaxial sampling, FIG. 3A, $A_{particle}$ was assumed to be circular. For the sampler facing downward, FIG. 3B, $A_{particle}$ was assumed to be elliptical.

$A_{air}$ and $A_{particle}$ were determined for the same flow rate, wind velocity, and wind orientation. As an example, $A_{air}$ for isoaxial sampling is 1.6 cm$^2$ for a flow rate of 2 1 min$^{-1}$ and a wind velocity of 20 cm s$^{-1}$. $A_{particle}$ from images of the smoke streams, obtained under the same condition, measured approximately 1.5 cm$^2$. For $\Theta=90°$, at a flow rate of 2 1 min$^{-1}$ and a wind velocity of 50 cm s$^{-1}$, the upstream projected elliptical cross-sectional area for the limiting stream surface was calculated to be 0.66 cm$^2$ while the smoke images under the same conditions resulted in $A_{particle}=0.70$ cm$^2$. Equality of $A_{air}$ and $A_{particle}$ within experimental accuracy, which was expected, confirms the suitability of the techniques used for the flow pattern visualization.

Visualization of the smoke streamlines over the prototype sampler showed negligible turbulence effects due to the inlet geometry. This qualitative observation demonstrates an important feature of the new inlet design. The flow into the inlet followed a smooth curve even when the prototype sampler was placed at 90° to the horizontal wind direction. This behavior shows an advantage over other types of sampler where the streamlines do not enter the inlet smoothly and may thus affect the aspiration efficiency.

Determination of Sampling Eficiency in a Wind Tunnel

This part of the laboratory evaluation was performed using a horizontal high-velocity aerosol wind tunnel. The performance characteristics of the sampler were compared with a widely used and commercially available personal breathing zone sampler used for workplace analysis (closed-face 25 mm personal sampling filter cassette with a 4 mm inlet).

Monodisperse particles of uranine (sodium fluorescein) with physical diameter 13.5, 20 and 30 $\mu$m (aerodynamic diameter $d_{ae}$=17, 26 and 38 $\mu$m) were used as test aerosols. The monodisperse particles were generated by means of a vibrating orifice aerosol generator. The available aerosol delivery system and the wind tunnel were modified for drying and transport of the large aerosol particles to the test section.

To confirm the size and shape of the generated aerosol particles, the test particles were first sampled onto a fibrous filter pad that was rigidly suspended in the test section. Since solid dry aerosols do not create stains on a fibrous filter pad, lack of staining confirmed that the particles were fully solidified. The solid particles were sized under an opticle microscope using a Porton graticule. The upstream aerosol concentration $C_o$, was determined with an isokinetic sharp-edged tubular sampler connected to a single particle optical counter. The number of particles determined by the optical counter was corrected for gravitational settling in the isokinetic sampler.

The new sampler and a standard 25 mm filter cassette were mounted in the test section at the same height as the isokinetic sampler. The aerosol concentrations in the wind tunnel were checked before and after sample collection. The particle concentration in the wind tunnel was stable with variations no greater than ±15%. Triplicate samples were collected for wind velocities ranging from 100 to 300 cm s$^{-1}$ and the flow rate in the samplers was maintained at 2 1 min$^{-1}$ throughout the experiments. The particles were collected in the samplers on polyvinyl chloride filters and were analyzed by means of a fluorometer. The sampled aerosol concentrations, $C_s$ were obtained for both samplers by dividing the number of collected particles by the sampled air volume. Concentration $C_o$ and $C_s$, and equation (1) were used to calculate the overall sampling efficiencies.

The sampling efficiency data for both samplers, tested at $\Theta$=0 and 90°, are shown in FIGS. 4*a*–4*f* with differing particle sizes. The vertical bars indicate the standard deviation of the overall sampling efficiency from the mean of each set of results.

For a wind velocity range of 100–300 cm sec$^{-1}$ and a particle size of $d_{ae}$=17 $\mu$m, the average overall sampling efficiency of the new sampler is 52% for isoaxial and 31% for 90° sampling, FIG. 4*a* and 4*b*. For the same sampling conditions and $d_{ae}$=26 and 38 $\mu$m, the respective averages are 47% and 20% (FIG. 4*c* and 4*d*), and 34% and 7% (FIG. 4*e* and 4*f*). There is no statically significant change (at the 95% confidence level) in sampling efficiency as a function of wind velocity. The overall sampling efficiency for the larger particles ($d_{ae}$=38 μm) could not be determined at the lowest wind velocity of 100 cm s$^{-1}$ because of excessive gravitational losses in the reference sampler. Although the new sampler shows a decrease in overall sampling efficiency with increasing particle size and sampling angle, the overall sampling efficiency remains essentially constant over the entire range of wind velocities for a given particle size and sampler orientation.

Microscopic Analysis of Filter Deposit

To study the distribution of large particles over the filter surface, samples were collected using the horizontal high-velocity aerosol wind tunnel. Uranine particles of $d_{ae}$=17 μm were generated, and two samples were taken with the new sampler and the 25 mm filter cassette at three different sampler orientations: Θ=0, downward at Θ=45° and downward at Θ=90°. The wind velocity was constant at 250 cm s$^{31\ 1}$. The collected samples were mounted on microscope slides by dissolving the filter using acetone vapor. The particles were counted under a bright-field light microscope with a computer-controlled stage so that specific coordinates could be chosen on the filter surface. The area of each microscope field was calculated to be 0.0404 cm$^2$. The particles were counted in four diametric directions. Each diameter was divided into 11 sections and particles were counted in the center of each section. The section near the edge of the filter was not taken into consideration because of particle losses near the filter edge. Two counts were recorded for each field. A single mean and its standard deviation were determined for all data with each of the two samplers oriented in one of the three positions.

Table 1 shows the relative standard deviations in count variation across the filters measured with the new sampler and the 25 mm filter cassette under limited conditions. It is seen that for isoaxial orientation the uniformity of filter deposition for the new sampler is more than twice that for the 25 mm filter cassette. The difference measured for the 45° orientation is not so significant but still indicates a preference for using the new device to obtain better filter deposit uniformity. No notable difference was found for the 90° orientation.

TABLE 1

| Sampler | Measured relative standard deviation (%) of particle count on the filter surface | | |
|---|---|---|---|
| | θ = 0[a] | θ = 45°[a] | θ = 90°[a] |
| Filter Cassette[b,c] | 44.6 | 28.2 | 33.9 |
| New Sampler[c] | 19.2 | 19.7 | 33.9 |

[a]θ = 0° (isoaxial), 45° (facing downward), 90° (facing downward).
[b]Closed-faced 25 mm cassette.
[c]Tested with uranine particles of $d_{ae}$ = 17 μm at $U_w$ = 250 cm s$^{-1}$.

For comparison, the relative standard deviation assuming Poisson statistic (absolute standard deviation=square root of count) was also calculated. For the new sampler, the relative standard deviation due to Poisson count statistics alone was found to be 22.5% at Θ=0, 17.7% at 45°, and 29.7% at 90°. These values of the Poisson count component of variability are approximately the same as the corresponding measured variabilities presented in Table 1. Thus, little of the measured variability in the new sampler is due to non-uniform deposits. For the filter cassette, the Poisson deviation was found to be 10.1% at Θ=0, 10.9% at 45°, and 27.8% at 90°. The larger measured variabilities at 0° and 45° (44.6% and 28.2%, respectively) indicate that the greater percentage of these variability levels due to non-uniform particle deposition on the filter. For both sampler at 90°, the low sampler loading contributed to high Poisson variability (29.7% for the new sampler and 27.8% for the filter cassette). In this case, it is difficult to make a judgement on the sample uniformity due to inadequate statistics. However, in the 90° case for the new sampler, the surface density of deposited particles was observed to be higher on the upstream side of the filter.

The distribution of particles on the filter of the 25 mm filter cassette is non-uniform for all three orientations tested. For isoaxial sampling the collection of particles was highest in the center region, while for non-isoaxial sampling the distribution was highly variable across the filter surface.

Conclusions from Laboratory Evaluation

Because the wind conditions do not remain constant in occupational and ambient air environments, sampling bias due to changing wind conditions should be minimal when sampling aerosols from such environments. Performance evaluations of the frequently used 25 mm filter cassette indicate a strong sampling efficiency dependence on wind magnitude and direction. By comparison, the experimental data collected with the sampler constructed according to the preferred embodiments indicate virtually no wind velocity dependence and much less wind direction dependence. The design of the new sampler is based on the aerodynamic quality of a bluff body which allows smooth flow over its surface in a fast moving wind. This flow pattern was confirmed visually using smoke stream tests. The pore diameter of the spherical shell can be used as the particle size limiting factor because of its ability to exclude particles that are approximately equal to or larger than its orifice size. Measurements of the filter deposits indicate that this inlet yields improved uniformity in particle distribution, an advantage when the filter is evaluated by a particle counting method.

We claim:
1. Method of collecting solid and liquid aerosols suspended in air comprising drawing said air through a sieve element having a partial substantially spherical shape with a subtended angle between 90 and 270 degrees and a porosity between 1% and 60%, said sieve element having a concave side and a convex side and including substantially uniformly spaced holes between 10 μm and 1 mm in diameter by applying a vacuum to said concave side of said sieve element, and collecting solid and liquid aerosols which pass through said sieve element in a chamber or on a filter.

2. Method of claim 1 wherein said partial substantially spherical shape of said sieve element is substantially hemispherical.

3. Method of claim 1 wherein said solid and liquid aerosols are collected in a chamber.

4. Method of claim 1 wherein said holes are substantially uniformly sized between 50 μm and 500 μm in diameter.

5. Method of claim 1 wherein said air is drawn through said sieve element at a flow rate between 0.1 and 300 liters per minute.

6. Method of claim 5 wherein the pressure drop across said sieve element is between about 0.04 inch and about 40 inches water gauge.

7. Method of claim 1 wherein said solid and liquid aerosols which pass through said sieve element are collected on a filter.

* * * * *